United States Patent [19]

Makino et al.

[11] Patent Number: 5,093,219

[45] Date of Patent: Mar. 3, 1992

[54] ELECTROPHOTOGRAPHIC PHOTORECEPTOR WITH ACETYLENE GROUP CONTAINING COMPOUND

[75] Inventors: Naonori Makino; Satoshi Hoshi; Katsugi Kitatani, all of Kanagawa, Japan

[73] Assignee: Fuji Photo Film Co., Ltd., Kanagawa, Japan

[21] Appl. No.: 569,052

[22] Filed: Aug. 17, 1990

[30] Foreign Application Priority Data

Aug. 17, 1989 [JP] Japan .................. 1-212081

[51] Int. Cl.$^5$ .................. G03G 5/047; G03G 5/06; G03G 5/09
[52] U.S. Cl. .................. 430/58; 430/59; 430/70; 430/71; 430/72; 430/73; 430/74; 430/75; 430/76; 430/78; 430/79; 430/83
[58] Field of Search .................. 430/58, 59, 70, 71, 430/72, 73, 74, 75, 76, 77, 78, 79, 83

[56] References Cited

U.S. PATENT DOCUMENTS

| | | | |
|---|---|---|---|
| 3,772,011 | 11/1973 | Guevara et al. | 430/56 X |
| 3,772,027 | 11/1973 | Luckey et al. | 430/87 X |
| 4,208,501 | 6/1980 | Yee et al. | 430/80 X |
| 4,220,747 | 9/1980 | Preziosi et al. | 522/174 X |
| 4,495,264 | 1/1985 | Takahashi et al. | 430/72 X |
| 4,504,559 | 3/1985 | Makino et al. | 430/76 X |
| 4,977,051 | 12/1990 | Ohno et al. | 430/70 X |
| 5,019,474 | 5/1991 | Makino et al. | 430/58 X |

*Primary Examiner*—Roland Martin
*Attorney, Agent, or Firm*—Sughrue, Mion, Zinn, Macpeak & Seas

[57] ABSTRACT

A novel electrophotographic photoreceptor is provided comprising a light-sensitive layer containing at least one of acetylene compounds represented by general formula (I) provided on an electrically conductive support:

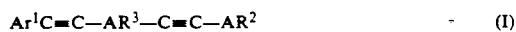

$$Ar^1C\equiv C-AR^3-C\equiv C-AR^2 \qquad (I)$$

wherein $Ar^1$ and $Ar^2$ each represents an aromatic carbon ring or aromatic heterocyclic group; and $Ar^3$ represents an arylene group, divalent condensed polycyclic aromatic group or divalent aromatic heterocyclic group.

21 Claims, No Drawings

ELECTROPHOTOGRAPHIC PHOTORECEPTOR WITH ACETYLENE GROUP CONTAINING COMPOUND

FIELD OF THE INVENTION

The present invention relates to an electrophotographic photoreceptor. More particularly, the present invention relates to an electrophotographic photoreceptor comprising a layer containing a novel charge-transporting compound or a novel photoconducting compound.

BACKGROUND OF THE INVENTION

As photoconducting materials to be incorporated in electrophotographic photoreceptors there have heretofore been used inorganic photoconductive substances such as selenium, cadmium sulfide, zinc oxide and amorphous silicon. These inorganic photoconductive substances are advantageous in that they have excellent electrophotographic properties. In particular, these inorganic photoconductive substances exhibit an excellent photoconductivity, charge acceptability in a dark place and insulating properties. On the contrary, however, these inorganic photoconductive substances have various disadvantages. For example, these photoreceptors are expensive to manufacture, can cause a pollution problem, have no flexibility and cannot withstand thermal or mechanical shock.

In recent years, electrophotographic photoreceptors comprising various organic photoconductive substances have been studied and proposed to eliminate these disadvantages of such inorganic photoconductive materials.

Most organic electrophotographic photoreceptors are lamination type photoreceptors having an electrically conductive support comprising at least two years, i.e., charge-generating layer which generates charge carriers upon exposure and charge-transporting layer which transports charge carriers. The charge-transporting layer essentially consists of a charge-transporting substance which transports charge carriers which have been generated in the charge-generating layer and then injected into the charge-transporting layer and a resin binder.

Such a charge-transporting substance is required (a) to sufficiently transmit light which has been absorbed by a charge-generating agent to allow the charge-generating substance to efficiently generate an electric charge, (b) to be sufficiently charged, and (c) to have a capability of having a charge carrier generated from the charge-generating substance efficiently injected thereinto to readily transport an electric charge.

There have been proposed many chargetransporting compounds such as triphenylmethane compounds as disclosed in JP-B-45-555 (the term "JP-B" as used herein means an "examined Japanese patent publication"), hydrazone compounds as disclosed in JP-B-55-42380, and JP-A-54-150128 (the term "JP-A" as used herein means an "unexamined published Japanese patent application" ), and triarylamine compounds as disclosed in JP-B-58-32372. Some photoreceptors comprising such a charge-transporting compound exhibit relatively excellent electrophotographic properties. However, these photoreceptors are disadvantageous in that they exhibit an insufficient sensitivity and a low durability to light or electric load and suffer from unstability and deterioration of properties upon repeated use. Therefore, these photoreceptors cannot sufficiently meet practical requirements. Thus, it has been desired to provide a charge-transporting compound which is more capable of transporting an electric charge and exhibits stable properties after a prolonged use.

As a result of extensive study, the inventors found that an acetylene compound represented by general formula (I) serves effectively as a charge-transporting compound in electrophotographic photoreceptors. Thus, the present invention was worked out.

SUMMARY OF THE INVENTION

It is therefore an object of the present invention to provide an electrophotographic photoreceptor comprising an electrophotographic light-sensitive layer containing a charge-transporting compound which fully transmits light of a wavelength suitable for the generation of an electric charge.

It is another object of the present invention to provide an electrophotographic photoreceptor comprising an electrophotographic light-sensitive layer which exhibits a low decay in potential in a dark place, a high sensitivity and little residual potential.

It is a further object of the present invention to provide an electrophotographic photoreceptor comprising a stable electrophotographic light-sensitive layer which is fast to oxygen derived from ozone produced by corona discharge, light and heat and exhibits little fluctuation in properties due to repeated use.

It is a yet another object of the present invention to provide an electrophotographic photoreceptor comprising an electrophotographic light-sensitive layer which contains an ecologically safe charge-transporting compound to provide safety of handling and disposal.

These and other objects of the present invention will become more apparent from the following detailed description and examples.

These objects of the present invention are accomplished with an electrophotographic photoreceptor, comprising a light-sensitive layer containing at least one of acetylene compounds represented by general formula (I) provided on an electrically conductive support:

$$Ar^1C \equiv C\text{-}Ar^3\text{-}C \equiv C\text{-}Ar^2 \qquad (I)$$

wherein $Ar^1$ and $Ar^2$ each represents an aromatic carbon ring or aromatic heterocyclic group; and $Ar^3$ represents an arylene group, divalent condensed polycyclic aromatic group or divalent aromatic heterocyclic group.

DETAILED DESCRIPTION OF THE INVENTION

The present acetylene compound will be further illustrated hereinafter.

Specific examples of an unsubstituted aromatic carbon ring group represented by $Ar^1$ or $Ar^2$, for example, include phenyl group, naphthyl group, anthryl group, pyrenyl group, acenaphthenyl group, and fluorenyl group. The carbon number of the aromatic group is from 6 to 20, preferably form 6 to 14.

The aromatic heterocyclic group represented by $Ar^1$ or $Ar^2$ is a 5 to 20 membered group which contains from 3 to 20 carbon atoms, the hetero atom of which is nitrogen, oxygen, sulfur, and selenium.

Specific examples of an unsubstituted aromatic heterocyclic group represented by $Ar^1$ or $Ar^2$, for example, include pyridine, thiophene, pyrrole, furan, benzofuran, benzothiophene, quinoline, carbazole, benzothiophene, and dibenzofuran.

Examples of the group represented by $Ar^3$, for example, include $C_{6-2}$, preferably $C_{6-12}$ arylene group such as phenylene, naphthalene, anthrylene, biphenylene, and terphenylene, divalent groups derived from $C_{9-20}$, preferably $C_{9-6}$ condensed polycyclic aromatic groups such as indene, fluorene, acenaphthene, azuylene, perylene, fluorenone, anthrone, anthraquinone, benzoanthrone, and isocoumarine, and divalent groups derived from 5 to 20 membered $C_{3-20}$ aromatic heterocyclic groups containing N, O, S, or Se as a hetero atom such as pyridine, quinoline, oxazole, thiazole, oxadiazole, benzoxazole, benzoimidazole, benzothiazole, benzotriazole, dibenzofurane, carbazole, phenothiazine, phenoxazine, and xanthene.

If $Ar^1$, $Ar^2$ and $Ar^3$ are aromatic carbon ring groups containing substituents, examples of such substituents include C1-8 alkyl group (e.g., methyl, ethyl, n-propyl), halogen atom (e.g., fluorine, chlorine, bromine, or iodine), cyano group, nitro group, hydroxyl group, carboxyl group, $C_{1-18}$ alkoxy group (e.g., methoxy, ethoxy, propoxy, butoxy), $C_{6-14}$ aryloxy group (e.g., phenoxy, o-tolyloxy, m-tolyloxy, p-tolyloxy, 1-naphthyloxy), dialkylamino group containing two $C_{1-8}$ alkyl groups (e.g., dimethylamino, diethylamino, dibutylamino), diarylamino group containing two $C_{6-10}$ aryl groups (e.g., diphenylamino, phenyltolylamino), N-alkyl-N-arylamino group containing $C_{1-8}$ alkyl group and $C_{6-10}$ aryl group (e.g., N-methyl-N-phenylamino, N-ethyl-N-phenylamino), $C_{6-14}$ aryl group (e.g., phenyl, naphthyl), trialkylsilyl group containing three $C_{1-6}$ alkyl groups (e.g., trimethylsilyl, t-butylmethylsilyl), halogenoalkyl group containing $C_{1-6}$ alkyl group (e.g., chloromethyl, trifluoromethyl), and $C_{1-6}$ alkylthio group (e.g., methylthio, ethylthio). Any number of such substituents can be bonded to any carbon in $Ar^1$, $Ar^2$ and $Ar^3$, and if more than one, the substituents may be the same or different.

Specific examples of acetylene compounds represented by the general formula (I) will be set forth below, but the present invention should not be construed as being limited thereto.

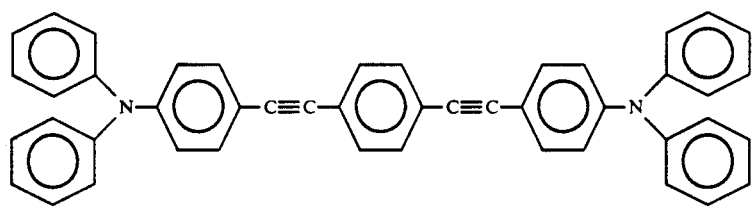

A-1

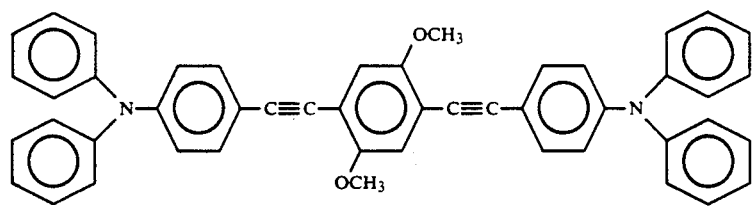

A-2

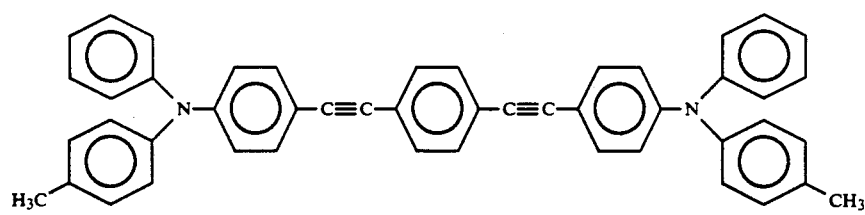

A-3

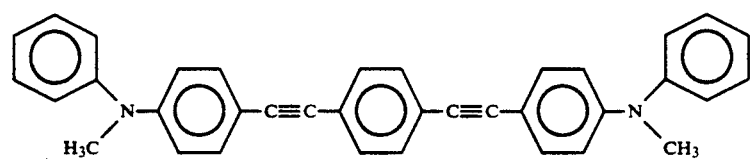

A-4

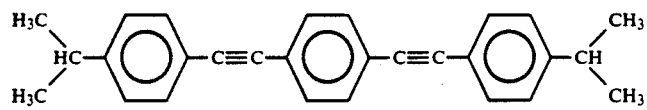

A-5

-continued
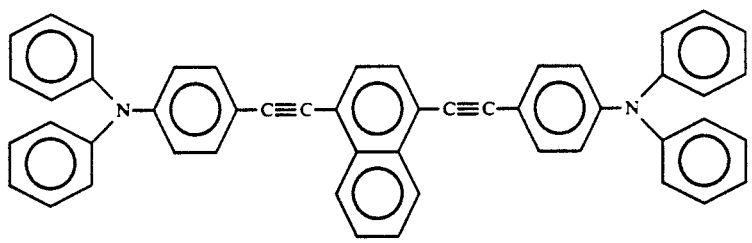
A-6
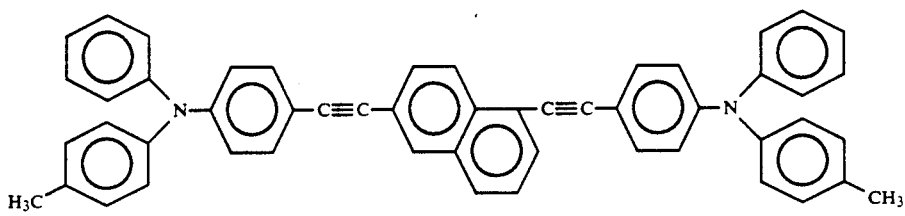
A-7
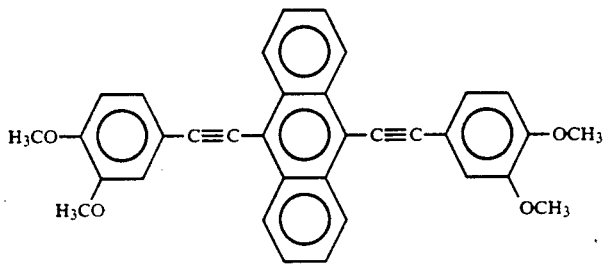
A-8
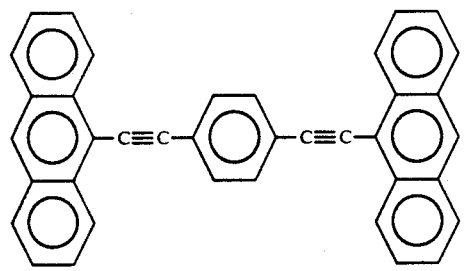
A-9
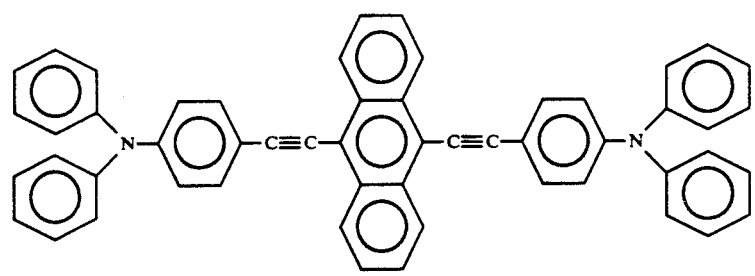
A-10
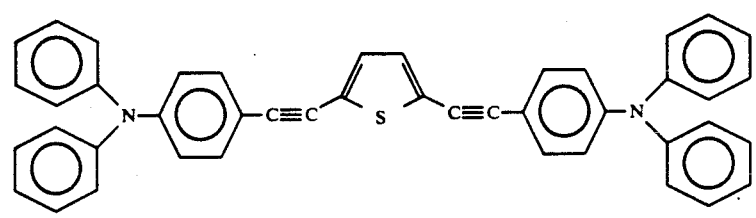
A-11

-continued
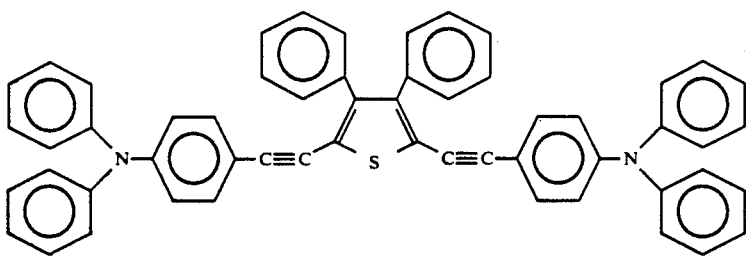
A-12
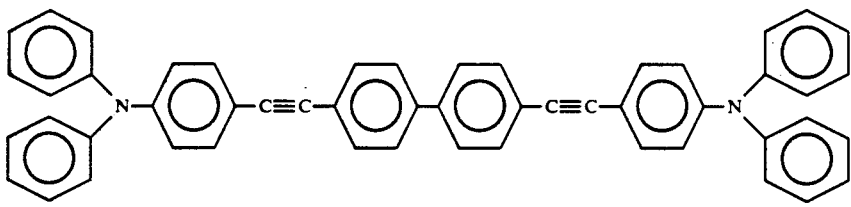
A-13
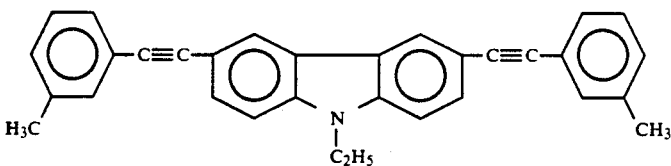
A-14
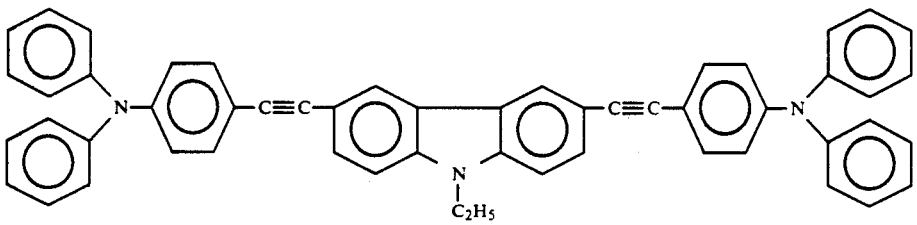
A-15
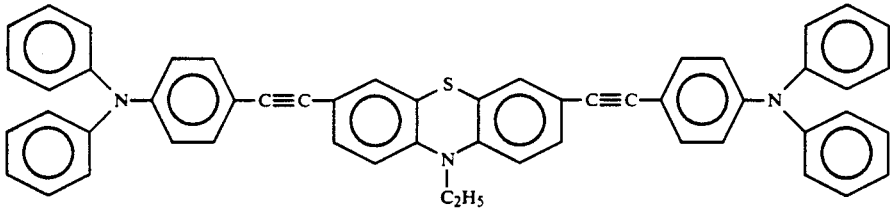
A-16
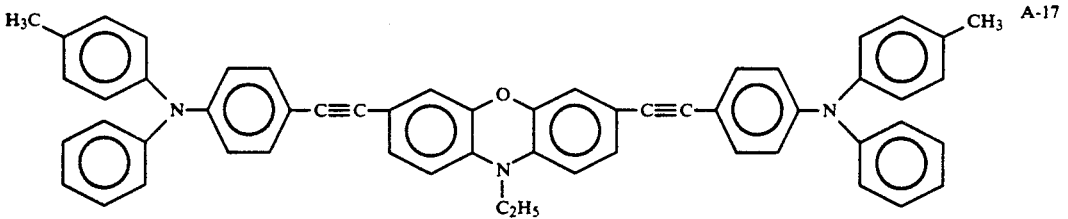
A-17
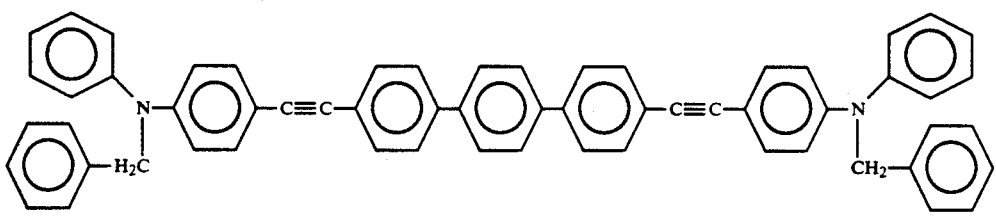
A-18

-continued
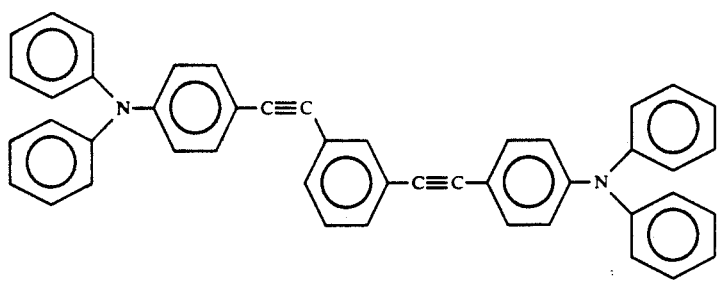
A-19
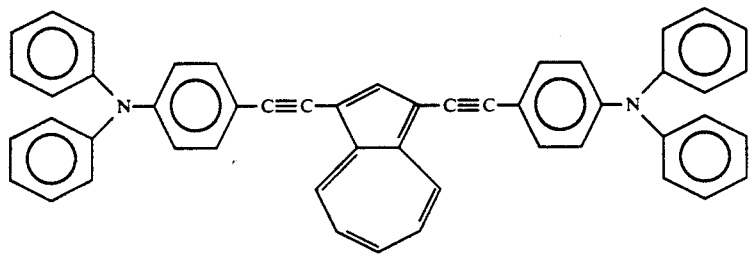
A-20
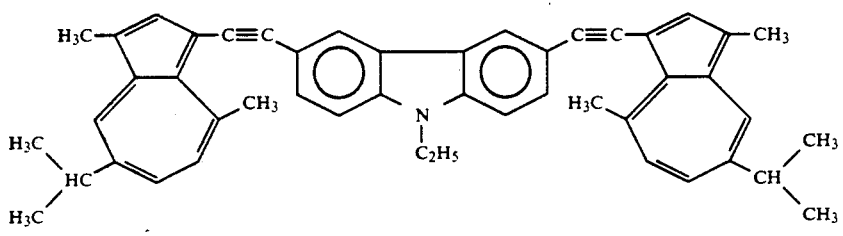
A-21
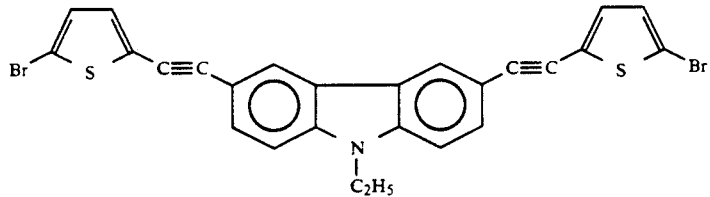
A-22
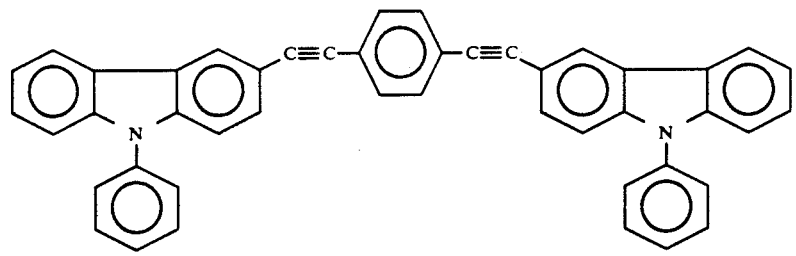
A-23
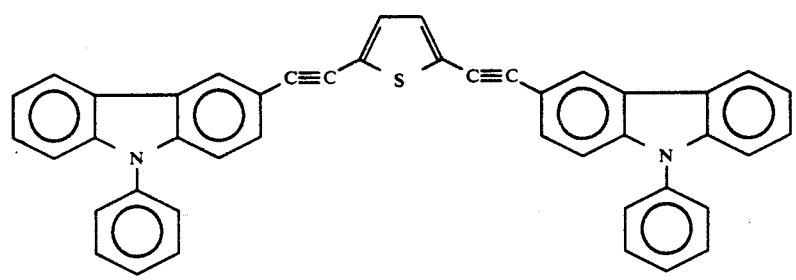
A-24

-continued

A-25

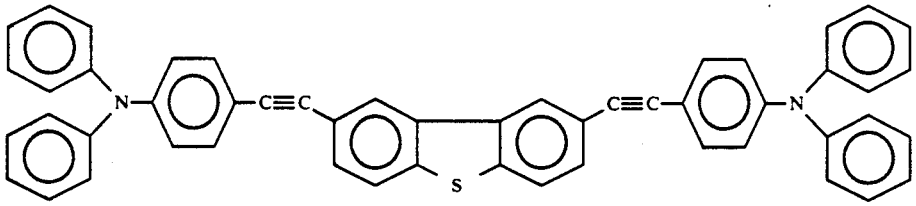

The preparation of the acetylene compound represented by general formula (I) can be typically accomplished by the following methods. For example, a compound represented by general formula (II) and a bisaldehyde represented by general formula (III) can be allowed to undergo reaction in an organic solvent such as DMF, DMSO and THF in the presence of a proper base (e.g., sodium hydride, sodium methoxide, potassium-t-butoxide) to produce the desired acetylene compound.

wherein $Ar^1$ is as defined in general formula (I); Z represents a separatable group such as tosyl group and halogen atom; and $R'$ represents a lower alkyl group such as methyl group and ethyl group.

wherein $Ar^3$ is as defined in general formula (I).

The synthesis of the compound of general formula (II) can be accomplished by the synthesis method proposed by Ikawa (Ikawa et al, Nihon Kagaku Kaishi, 1974, (6), 1093).

The acetylene compound of the present invention can be incorporated in any of electrophotographic photoreceptors comprising an electrically conductive support in the following embodiments (I), (II), (III) and (IV):

(I) Single-layer photoreceptor comprising a charge-generating compound dispersed in a charge-transporting medium consisting of an acetylene compound and a binder;

(II) Laminated photoreceptor comprising a charge-generating layer containing a charge-generating compound and a charge-transporting layer containing an acetylene compound;

(III) Laminated photoreceptor comprising a charge-generating layer containing a charge-generating compound and an acetylene compound and a charge-transporting layer containing a charge-transporting compound; and (IV) Single-layer photoreceptor containing both a sensitizing dye and an acetylene compound.

In embodiment (I), the acetylene compound form a charge-transporting medium with a binder (or a binder and a plasticizer) while a charge-generating compound such as inorganic or organic pigment generates an electric charge. In this case, the charge-transporting medium is capable of mainly accepting and transporting a charge carrier which is generated by a charge-generating compound. This is basically conditioned that the charge-generating compound and the acetylene compound do not have the same absorption wavelength mainly in the visible light range. This is because it is necessary to allow light to reach the surface of the charge-generating compound to allow the charge-generating compound to efficiently produce a charge carrier. The present acetylene compound has little absorption in the visible light range. If the present acetylene compound is used in combination with a charge-generating compound which normally absorbs visible light to produce a charge carrier, it serves as an effective charge-transporting compound.

In embodiment (II), the light which has passed through the charge-transporting layer reaches the charge-generating layer where a charge carrier is produced. The charge carrier thus produced is injected into and transported by the charge-transporting layer. This mechanism is the same as that of embodiment (I) in that a charge carrier is produced by the charge generating compound and an electric charge is transported by the charge-transporting medium (mainly by the present acetylene compound).

In embodiment (III), the mechanism of charge generation and transportation is the same as that of embodiment (II). In general, however, laminated photoreceptors are susceptible to drop in surface potential and increase in residual potential after repeated use because the charge carrier migrates at a low speed in the charge-generating layer. These troubles can be eliminated by incorporating an acetylene compound in the charge-generating layer to raise the rate at which the charge carrier migrates in the charge-generating layer.

In embodiment (IV), the acetylene compound serves as a photoconducting compound for the production and transportation of a charge carrier required for decay by light. However, since the acetylene compound has little or no absorption in the visible light range, it is necessary that a sensitizing dye having absorption in the visible light range be incorporated in the system for sensitization to form images in the visible light range.

The preparation of embodiment (I) can be accomplished by a process which comprises dispersing finely divided grains of a charge-generating compound in a solution of an acetylene compound and a binder, coating the dispersion on an electrically conductive support, and then drying the material. The preparation of embodiment (II) can be accomplished by vacuum-depositing a charge-generating compound on an electrically conductive support or dispersing finely divided grains of a charge-generating compound in a proper solvent optionally containing a binder, coating the dispersion on a support, drying the coated material, and then optionally finishing the surface of the layer by a proper process such as buffing or otherwise adjusting the thickness of the film, coating a solution containing an acetylene compound and a binder thereon, and drying the coated material. The preparation of embodiment (III) can be accomplished by dispersing finely divided grains of a charge-generating agent and an acetylene compound in a proper solvent optionally containing a binder to obtain a dispersion, coating the dispersion on an electrically conductive support, drying the coated material, and then optionally finishing the surface of the layer by a proper process such as buffing or otherwise adjusting the thickness of the film, coating a solution containing an acetylene compound and a binder thereon, and drying the coated material. The preparation of embodiment (IV) can be accomplished by dissolving a sensitizing dye in a solution of an acetylene compound and a binder, coating the solution on an electrically conductive support, and then drying the material.

Examples of an electrically conductive support to be incorporated in the present electrophotographic photoreceptor include plate of metal such as aluminum, copper and zinc, material comprising a sheet or film of plastic such as polyester with an electrically conductive material such as aluminum, indium oxide, tin oxide and copper iodide vacuum-evaporated or dispersion-coated thereon, and paper treated with an electrically conductive material.

The coating of the coating solution can be accomplished by ordinary means such as doctor blade coating process, wire bar coating process, applicator coating process, spray coating process, dip coating process and extrusion coating process.

In embodiment (I), the thickness of the light-sensitive layer is in the range of 1 to 50 $\mu$m, preferably 5 to 20 $\mu$m. In embodiments (II) and (III), the thickness of the charge-generating layer is in the range of 5 $\mu$m or less, preferably 2 $\mu$m or less, and the thickness of the charge-transporting layer is in the range of 3 to 50 $\mu$m, preferably 10 to 25 $\mu$m. In embodiment (IV), the thickness of the charge-transporting layer is in the range of 2 to 40 $\mu$m, preferably 5 to 20 $\mu$m.

In embodiment (I), the proportion of the acetylene compound in the light-sensitive layer is in the range of 10 to 95% by weight, preferably 30 to 90% by weight of the total weight of said layer, and the proportion of the charge-generating compound in the light-sensitive layer is in the range of 1 to 50% by weight, preferably 1 to 20% by weight. In embodiments (II) and (III), the proportion of the acetylene compound in the charge-transporting layer is in the range of 10 to 95% by weight, preferably 30 to 90% by weight of the total weight of said layer. In embodiment (II), the proportion of the charge-generating compound in the charge-generating layer is in the range of 10 to 100% by weight, preferably 30 to 90% by weight of the total weight of said layer. The charge-generating layer in embodiment (III) comprises a charge-generating compound in an amount of 0.01 to 90% by weight, preferably 0.05 to 70% by weight, and an acetylene compound in an amount of 0.1 to 70% by weight, preferably 0.05 to 50% by weight of the total weight of said layer. In embodiment (IV), the proportion of the acetylene compound in the light-sensitive layer is in the range of 10 to 95% by weight, preferably 25 to 80% by weight of the total weight of said layer.

Furthermore, the binder can be used in combination with a plasticizer in embodiments (I) to (IV).

As a binder to be incorporated in the present photoreceptor there may be preferably used a hydrophobic high dielectric electrically insulating film-forming high molecular polymer. Specific examples of such a high molecular polymer will be set forth below, but the present invention should not be construed as being limited thereto.

Polycarbonate, polyester, polyester carbonate, polysulfone, methacrylic resin, acrylic resin, polyvinylchloride, polyvinylidene chloride, polystyrene, polyvinyl acetate, styrene-butadiene copolymer, vinylidene chloride-acrylonitrile copolymer, vinyl chloride-vinyl acetate copolymer, vinyl chloride-vinyl acetate-maleic anhydride copolymer, silicone resin, silicone-alkyd resin, phenol-formaldehyde resin, styrene-alkyd resin, styrene-maleic anhydride copolymer, phenoxy resin, polyvinylbutyral resin, poly-N-vinylcarbazole.

These resin binders can be used singly or in admixture.

Examples of plasticizers which can be incorporated in the present invention together with such a binder include biphenyl, biphenylchloride, o-terphenyl, p-terphenyl, dibutyl phthalate, dimethyl glycol phthalate, dioctyl phthalate, triphenylphosphoric acid, chlorinated paraffin, and dilauryl thiodipropionate.

Examples of sensitizing dye which can be incorporated in the photoreceptor of type (IV) include triallyl methane dye such as Brilliant Green, Victorian Blue B, Methyl Violet, Crystal Violet and Acid Violet 6B, hexanthene dye such as Rhodamine B, Rhodamine 6G, Rhodamine G Extra, Eosine S, Erythorosine, Rose Bengal and Fluoresceine, thiazine dye such as Methylene Blue, astrazone dye such as C.I. Basic Violet 7 (e.g., C. I. 48020), cyanine dye, and pyrilium dye such as 2,6-diphenyl-4-(N, N-dimethylaminophenyl)-thapyrilium perchlorate and benzopyrilium salt (as described in JP-B-48-25658).

In order to improve the surface characteristics of the electrophotographic photoreceptor, a silicone oil, fluorine surface active agent or the like may be used.

Examples of charge-generating compounds which can be incorporated in the present photoreceptor include inorganic photoconducting materials such as selenium, selenium-tellurium, cadmium sulfide and zinc oxide, and organic photoconducting materials as set forth below: (1) Monoazo, bisazo and trisazo pigments as described in U.S. Pat. Nos. 4,436,800, and 4,439,506, JP-A-47-37543, JP-A-58-123541, JP-A-58-92-192042, JP-A-58-19263, JP-A-59-78356, JP-A-60-179746, JP-A-61-148453, and JP-A-61-238063, and JP-B-60-5941, and JP-B-60-45664;

(2) Phthalocyanine pigments such as metallic phthalocyanine or nonmetallic phthalocyanine as described in U.S. Pat. Nos. 3,397,086, and 4,666,802;

(3) Perylene pigments as described in U.S. Patent 3,371,884;

(4) Indigo and thioindigo derivatives as described in U.S. Pat. No. 2,237,680;

(5) Quinacridone pigments as described in British Patent No. 2,237,679;

(6) Polycyclic quinone pigments as described in British Patent No. 2,237,678, and JP-A-59-184348, and JP-A-62-28738;

(7) Bisbenzimidazole pigments as described in JP-A-47-30331;

(8) Squalium salt pigments as described in U.S. Pat. Nos. 4,396,610, and 4,644,082; and (9) Azulenium salt pigments as described in JP-A-59-53850, and JP-A-61-212542.

These organic photoconducting materials can be used singly or in combination.

Preferred among these charge-generating compounds are azo dyes.

In the present invention, as charge-transporting compounds there can be used acetylene compounds represented by general formula (I) and other chargetransporting compounds, singly or in combination. Chargetransporting compounds other than the present acetylene compounds to be incorporated in the chargetransporting layer can be classified into two kinds of compounds: compounds which transport electrons and compounds which transport positive holes. The electrophotographic photoreceptor of the present invention can comprise either or both the two types of compounds.

As such a compound which transports electrons there can be used a compound containing an electron attracting group. Examples of such a compound include 2,4,7-trinitro-9-fluorenone, 2,4,5,7-tetranitro-9-fluorenone, 9-dicyanomethylene-2,4,7-trinitrofluorenone, 9-dicyanomethylene-2,4,5,7-tetranitrofluorenone, tetranitrocarbazole, chloranil, 2,3-dichloro-5,6-dicyanobenzoquinone, 2,4,7-trinitro-9, 10-phenanthrenequinone, tetrachlorophthalic anhydride, tetracyanoethylene, and tetracyanoquinodimethane.

As such a compound which transports positive holes there can be used a compound containing an electron-donating group.

Examples of such a compound having a high molecular weight include:

(a) Polyvinyl carbazoles and derivatives thereof as described in JP-B-34-10966;

(b) Vinyl polymers as described in JP-B-43-18674 and JP-B-43-19192 such as polyvinyl pyrene, polyvinyl anthracene, poly-2-vinyl-4-(4'-dimethylaminophenyl)-5-phenyloxazole and poly-3-vinyl-N-ethylcarbazole;

(c) Polymers as described in JP-B-43-19193 such as copolymers of styrene with polyacenaphthylene, polyindene or acenaphthylene;

(d) Condensed resins as described in JP-B-56-13940 such as pyrene-formaldehyde resin, bromopyrene-formaldehyde resin and ethylcarbazole-formaldehyde resin; and (e) Various triphenylmethane polymers as described in JP-A-56-90883 and JP-A-56-161550.

Examples of such a compound having a low molecular weight include:

(f) Triazole derivatives as described in U.S. Pat. No. 3,112,197;

(g) Oxadiazole derivatives as described in U.S. Pat. No. 3,189,447;

(h) Imidazole derivatives as described in JP-B-37-16096;

(i) Polyarylalkane derivatives as described in U.S. Pat. Nos. 3,615,402, 3,820,989 and 3,542,544, JP-B-45-555 and JP-B-51-10983, and JP-A-51-93224, JP-A-55-108667, JP-A-55-156953, JP-A-56-36656;

(j) Pyrazoline derivatives and pyrazolone derivatives as described in U.S. Pat. Nos. 3,180,729 and 4,278,746, and JP-A-55-88064, JP-A-55-88064, JP-A-55-88065, JP-A-49-105537, JP-A-55-51086, JP-A-56-80051, JP-A-56-88141, JP-A-57-45545, JP-A-54-112637 and JP-A-55-74546;

(k) Phenylenediamine derivatives as described in U.S. Pat. Nos. 3,615,404, JP-B-51-10105, JP-B-46-3712 and JP-B-47-28336, and JP-A-54-83435, JP-A-54-110836 and JP-A-54-119925;

(l) Arylamine derivatives as described in U.S. Pat. Nos. 3,567,450, 3,180,703, 3,240,597, 3,658,520, 4,232,103, 4,175,961 and 4,012,376, West German Patent DAS) 1,110,518, JP-B-49-35,702 and JP-B-39-27577, and JP-A-55-144250, JP-A-56-119,132 and JP-A-56-2437;

(m) Amino-substituted chalcone derivatives as described in U.S. Pat. No. 3,526,501;

(n) N,N-bicarbazyl derivatives as described in U.S. Pat. No. 3,542,546;

(o) Oxazole derivatives as described in U.S. Pat. No. 3,257,203;

(p) Styrylanthracene derivatives as described in JP-A-56-46234;

(q) Fluorenone derivatives as described in JP-A-54-110837;

(r) Hydrazone derivatives as described in U.S. Pat. No. 3,717,462, and JP-A-54-59143 (U.S. Pat. No. 4,150,987), JP-A-55-52063, JP-A-55-52064, JP-A-55-46760, JP-A-55-85495, JP-A-57-11350, JP-A-57-148749 and JP-A-57-104144;

(s) Benzidine derivatives as described in U.S. Pat. Nos. 4,047,948, 4,047,949, 4,256,990, 4,273,846, 4,299,897 and 4,306,008; and (t) Stilbene derivatives as described in JP-A-58-190953, JP-A-59-95540, JP-A-59-971148, JP-A-59-195658 JP-A-62-36674.

In the present invention, the electric charge carrier-transporting compounds should not be construed as being limited to those belonging to compound groups (a) to (t). All electric charge carrier-transporting compounds which have heretofore been known can be used.

In the preparation of the present electrophotographic photoreceptor, additives such as sensitizer can be incorporated in the charge-generating layer and charge-transporting layer. Alternatively, a charge-transporting compound can be incorporated in the charge-generating layer.

Examples of such a sensitizer include chloranil, tetracyanoethylene, methyl violet, Rhodamine B, cyanine dye, melocyanine dye, pyrilium dye, and thiapyrilium dye.

In the present electrophotographic photoreceptor, an adhesive layer or barrier layer can be optionally provided between the electrically conductive support and the light-sensitive layer. As examples of materials to be incorporated in these layers there can be used polymers such as the above-described binder. Other examples of materials to be incorporated in these layers include gelatin, casein, polyvinyl alcohol, ethyl cellulose, carboxymethyl cellulose, vinylidene chloride polymer latexes as described in JP-A-84247, styrenebutadiene polymer latexes as described in JP-A-59-114544, and aluminum oxide. The thickness of these layers is preferably in the range of 1 $\mu$m or less.

The present electrophotographic photoreceptor has been described in detail. The present electrophotographic photoreceptor generally exhibits a high sensitivity and a small change in the electrophotographic properties after repeated use.

The present electrophotographic photoreceptor can be widely used in electrophotographic copying machines as well as in the field of photoreceptors for printers using laser, CRT, LED or the like as light source.

The present invention will be further described in the following examples, but the present invention should not be construed as being limited thereto.

EXAMPLE 1

Selenium was vacuum-deposited on a grained aluminum plate having a thickness of about 300 $\mu$m to a thickness of 0.4 $\mu$m to form a charge-generating layer thereon. A solution of 10 parts by weight of an exemplified acetylene compound represented by general formula (A-1) and 10 parts by weight of a polycarbonate of bisphenol A (Panlite K-1300, available from Teijin Limited) in 130 parts by weight of dichloromethane was coated on the material by means of an applicator. The material was then dried to form a charge-transporting layer having a thickness of about 14 μm.

The electrophotographic photoreceptor thus prepared was then evaluated for electrophotographic properties in a static process by means of a static copying paper tester (Kawaguchi Denki Seisakusho K.K.'s Model SP-428). Specifically, the photoreceptor was first measured for surface potential Vo left after being corona-charged (−5 kv) over 5 seconds and then being stored in a dark place over 10 seconds. The photoreceptor was then exposed to light from a tungsten lamp with a color temperature of 2,854° K in such a manner that the illuminance on the surface of the photoreceptor reached 2 lux. The photoreceptor was then measured for sensitivity (exposure for half life: E50).

The results were Vo = −810V, and E50 = 1.3 lux.sec.

EXAMPLES 2 TO 6

Two-layer electrophotographic photoreceptors were prepared in the same manner as in Example 1 except that the acetylene compound (A-1) was replaced by those set forth in Table 1. These specimens were then measured for surface potential Vo by negative charging and exposure for half life E50 in the same manner as in Example 1. The results are set forth in Table 1.

TABLE 1

| Example No. | Acetylene Compound No. | Vo (−V) | E50 (lux · sec) |
| --- | --- | --- | --- |
| 2 | (A-3) | 790 | 1.2 |
| 3 | (A-6) | 820 | 1.4 |
| 4 | (A-10) | 800 | 1.5 |
| 5 | (A-16) | 800 | 1.4 |
| 6 | (A-19) | 780 | 1.7 |

EXAMPLE 7

5 parts by weight of 8 type copper phthalocyanine were subjected to ultrasonic dispersion in 660 parts of dichloromethane. 40 parts by weight of a polycarbonate of bisphenol A (Panlite K-1300) and 40 parts of the exemplified acetylene compound (A-3) were dissolved in the dispersion to prepare a coating solution. The coating solution thus prepared was then coated on an electrically conductive support (support comprising a film of indium oxide vacuum-deposited on a 100-μm thick polyethylene terephthalate film and a surface resistivity of $10^3$ Ω) by means of a wire round rod, and then dried to obtain a photoreceptor having a thickness of about 10 μm.

The photoreceptor was then measured for surface potential Vo developed after being corona-charged at +5 KV over 3 seconds and stored in a dark place over 10 seconds and exposure for half life E50 at an illuminance of 2 lux. The results were Vo = +550V and E50 = 3.5 lux.sec.

EXAMPLE 8 AND COMPARATIVE EXAMPLES 1 AND 2

2 parts by weight of a trisazo pigment represented by general formula (V) and 2 parts by weight of a polyester resin (Vylon 200, available from Toyobo Co., Ltd.) were subjected to dispersion in 7 parts by weight of tetrahydrofuran in a ball mill over 12 hours. The dispersion thus prepared was coated on an electrically conductive support (support comprising a film of aluminum vacuum-deposited on a 75-μm thick polyethylene terephthalate film; Metalme 75TS, available from Toray Industries Inc.) and then dried to obtain a charge-generating layer having a thickness of about 0.5 μm.

A solution of 3.6 parts by weight of the exemplified acetylene compound (A-1) and 4 parts by weight of a polycarbonate of bisphenol A (Panlite K-1300, available from Teijin Limited) in a solvent consisting of 13.3 parts by weight of dichloromethane and 26.6 parts by weight of dichloroethane was coated on the charge-generating layer by means of an applicator and dried to form a 17-μm thick charge-transporting layer thereon. Thus, an electrophotographic photoreceptor comprising a light-sensitive layer consisting of two layers was prepared.

Trisazo Pigment (V)

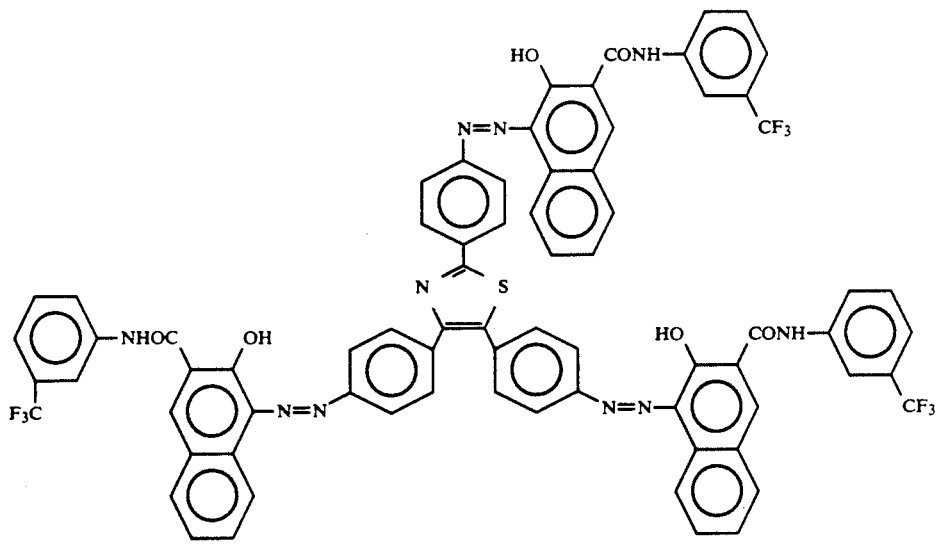

Comparative Photoreceptor Specimens 1 and 2 (Comparative Examples 1 and 2) were prepared in the same manner as described above except that acetylene compound (A-1) was replaced by the compounds represented by general formulae (B-1) and (B-2), respectively, as charge-transporting agents.

background and marked fog and black spots on the white background.

TABLE 2

| | | 1st Time | | | 3000th Time | | |
|---|---|---|---|---|---|---|---|
| | $V_s$ (−V) | $V_o$ (−V) | E50 (lux · sec) | $V_R$ (−V) | $V_s$ (−V) | $V_o$ (−V) | E50 (lux · sec) | $V_R$ (−V) |
| Example 8 | 960 | 830 | 1.2 | 0 | 920 | 780 | 1.2 | 0 |
| Comp. Ex. 1 | 950 | 650 | 2.6 | 5 | 660 | 480 | 4.2 | 20 |
| Comp. Ex. 2 | 900 | 800 | 3.5 | 20 | 830 | 710 | 4.9 | 55 |

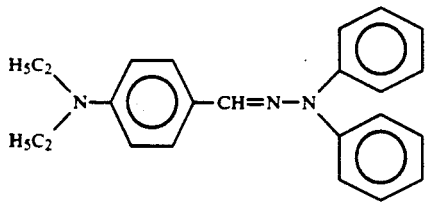

(B-1)

EXAMPLES 9 TO 20

Two-layer electrophotographic photoreceptors were prepared in the same manner as in Example 8 except that as charge-transporting compounds there were used acetylene compounds as set forth in Table 3. These electrophotographic photoreceptors were then measured for E50, $V_s$, $V_o$, and $V_R$ in the same manner as in Example 1. The results are set forth in Table 3.

TABLE 3

| Example No. | Acetylene Compound No. | 1st Time | | | | 3000th Time | | | |
|---|---|---|---|---|---|---|---|---|---|
| | | $V_s$ (−V) | $V_o$ (−V) | E50 (lux · sec) | $V_R$ (−V) | $V_s$ (−V) | $V_o$ (−V) | E50 (lux · sec) | $V_R$ (−V) |
| 9 | (A-2) | 980 | 860 | 1.6 | 0 | 930 | 820 | 1.7 | 4 |
| 10 | (A-3) | 930 | 820 | 1.5 | 1 | 870 | 765 | 1.6 | 1 |
| 11 | (A-4) | 910 | 790 | 1.5 | 0 | 880 | 750 | 1.5 | 1 |
| 12 | (A-6) | 900 | 750 | 1.7 | 1 | 840 | 710 | 1.7 | 1 |
| 13 | (A-7) | 890 | 780 | 1.6 | 0 | 840 | 740 | 1.6 | 1 |
| 14 | (A-10) | 930 | 800 | 1.5 | 1 | 910 | 780 | 1.5 | 2 |
| 15 | (A-11) | 940 | 840 | 1.4 | 0 | 900 | 810 | 1.4 | 1 |
| 16 | (A-13) | 930 | 790 | 1.5 | 0 | 900 | 770 | 1.5 | 1 |
| 17 | (A-15) | 890 | 770 | 1.8 | 0 | 840 | 750 | 1.8 | 0 |
| 18 | (A-18) | 950 | 820 | 1.5 | 0 | 900 | 770 | 1.6 | 2 |
| 19 | (A-20) | 900 | 760 | 1.3 | 0 | 830 | 700 | 1.4 | 2 |
| 20 | (A-23) | 970 | 830 | 1.7 | 0 | 950 | 780 | 1.7 | 1 |

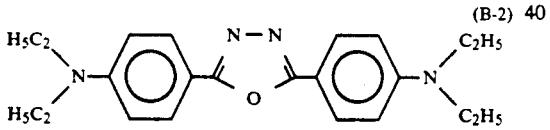

(B-2)

These electrophotographic photoreceptors thus prepared were then evaluated for electrophotographic properties in a static process by means of a static copying paper tester (Kawaguchi Denki Seisakusho K.K.'s Model SP-428). Specifically, these photoreceptors were first measured for surface potential $V_s$ developed shortly after being corona-charged at −6 kv and surface potential $V_o$ developed after being stored in a dark place over 30 seconds. These photoreceptors were then exposed to light from a tungsten lamp in such a manner that the illuminance on the surface of the photoreceptor reached 3 lux. These photoreceptors were then measured for exposure E50 required to reduce the surface potential to half the initial surface potential and residual surface potential $V_R$ left after 30-second exposure. These measurements were repeated 3,000 times. The results are set forth in Table 2.

These photoreceptors were then used in a copying machine (SF-750 available from Sharp Corporation) to evaluate image quality. The photoreceptor obtained in Example 1 provided a sharp uniform image while the photoreceptors obtained in Comparative Examples 1 and 2 provided images having white spots on the black

EXAMPLE 21 And COMPARATIVE EXAMPLE 3

5 parts by weight of a disazo pigment represented by general formula (VI) was subjected to dispersion in a solution of 3 parts by weight of the exemplified acetylene compound (A-4) and 5 parts by weight of a polyester resin (Vylon 200, available from Toyobo Co., Ltd.) in 44 parts by weight of tetrahydrofuran in a ball mill over 12 hours. The dispersion thus prepared was then coated on an electrically conductive support (support comprising a film of aluminum vacuum-deposited on a 75-μm thick polyethylene terephthalate film; Metalme 75TS, available from Toray Industries Inc.) by means of a wire round rod, and then dried to obtain a charge-generating layer having a thickness of about 0.5 μm.

A solution of 3.6 parts by weight of a hydrazone compound represented by general formula (VII) and 4 parts by weight of a polycarbonate of bisphenol A (Panlite K-1300, available from Teijin Limited) in a solvent consisting of 13.3 parts by weight of dichloromethane and 26.6 parts by weight of dichloroethane was coated on the charge-generating layer by means of an applicator to form a 17-μm thick charge-transporting layer thereon. Thus, an electrophotographic photoreceptor comprising a light-sensitive layer consisting of two layers was prepared.

Comparative Photoreceptor Specimen 3 (Comparative Example 3) was prepared free of acetylene compound (A-4) in the charge-generating layer.

These photoreceptrs were measured for E50, Vs, Vo and VR in the same manner as in Example 1. The results are set forth in Table 4.

As shown in Table 4, the photoreceptor obtained in Example 21 comprising the acetylene compound exhibits a higher sensitivity and a higher stability in potential after repeated use than the photoreceptor in Comparative Example 3.

As a result, a sharp positive toner image was able to be obtained.

The specimen was then heated to a temperature of 100° C. over 30 seconds to fix the toner image. The printing plate material was immersed in an etching solution obtained by dissolving 70 g of sodium metasilicate hydrate in 140 ml of glycerin, 550 ml of ethylene glycol and 150 ml of ethanol over 1 minute. The printing plate

TABLE 4

Disazo Pigment (VI)

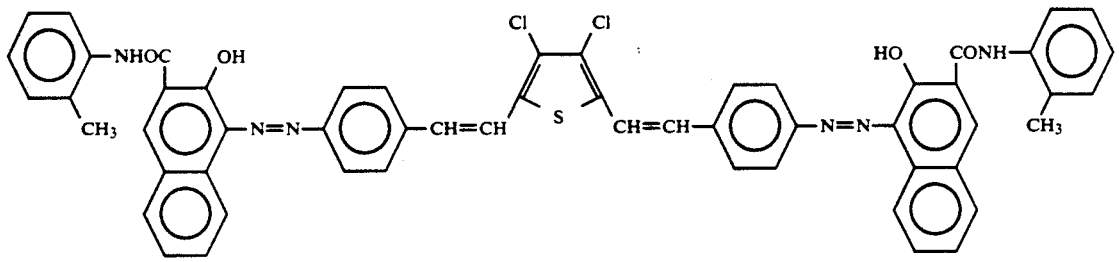

Hydrazone compound (VII)

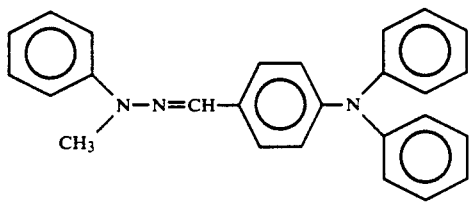

|  | 1st Time | | | | 3000th Time | | | |
| --- | --- | --- | --- | --- | --- | --- | --- | --- |
|  | Vs (−V) | Vo (−V) | E50 (lux · sec) | V$_R$ (−V) | Vs (−V) | Vo (−V) | E50 (lux · sec) | V$_R$ (−V) |
| Example 21 | 960 | 830 | 1.6 | 0 | 920 | 800 | 1.6 | 0 |
| Comp. Ex. 3 | 930 | 800 | 2.5 | 5 | 510 | 400 | 2.9 | 35 |

EXAMPLE 22

5 parts by weight of the trisazo compound (V) as used in Example 8, 40 parts by weight of the exemplified acetylene compound (A-1) and 100 parts of a copolymer of benzyl methacrylate and methacrylic acid ([n] 30° C. in methyl ethyl ketone: 0.12; methacrylic acid content: 32.9%) were added to 660 parts by weight of dichloromethane. The mixture was then subjected to dispersion in a ball mill over 12 hours. The dispersion was then coated on a 0.25-mm thick grained aluminum plate, and dried to prepare an electrophotographic printing plate material comprising a 6-μm thick electrophotographic light-sensitive layer.

The specimen was then subjected to corona discharge at +6 KV in a dark place so that the light-sensitive layer was charged at a surface potential of 500V. The specimen was then exposed to light from a tungsten lamp with a color temperature of 2,854° K. in such a manner that the illuminance on the surface of the specimen reached 2.0 lux. As a result, the specimen exhibited a half life exposure E50 of 2.7 lux.sec.

The specimen was then charged at a surface potential of +500V in a dark place. The specimen was then imagewise exposed to light with a transparent original of positive image brought into close contact thereto. The specimen was then immersed in a liquid developer comprising 1 l of Isopar H (petroleum solvent produced by Esso Standard), 5 g of finely dispersed polymethyl methacrylate (toner) and 0.01 g of soybean oil lecithin.

material was washed in a water flow with light brushing to remove the light-sensitive layer on the portion free of the toner. Thus, the desired printing plate was obtained.

The printing plate thus prepared was then used for printing by means of Hamada Star 600 CD Offset Printer. As a result, 50,000 sheets of extremely sharp printed matters free of any stain on the background were obtained.

EXAMPLE 23

8 parts by weight of the exemplified acetylene compound (A-1), 10 parts by weight of a polycarbonate of bisphenol A (Panlite K-1300) and 0.12 parts by weight of an astrazone dye represented by the following general formula were dissolved in 110 parts by weight of dichloromethane to prepare a coating solution.

The coating solution was then coated on an electrically conductive transparent support (support comprising a film of indium oxide vacuum-deposited on a 100-μm thick polyethylene terephthalate film and a surface resistivity of $10^3$ Ω) by means of a wire round rod, and then dried to obtain a photoreceptor having a thickness of about 10 μm.

The photoreceptor was then positively charged by corona discharge at +5 KV. The photoreceptor was then measured for E50 in the same manner as in Example 1. As a result, E50 was 10.5 lux.sec.

Astrazone Dye

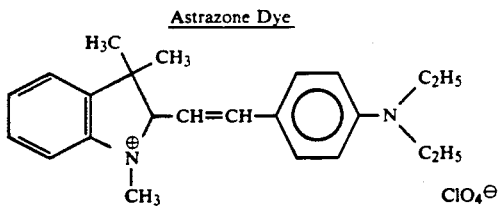

The use of the present acetylene compound as charge-transporting compound provides an electrophotographic photoreceptor having a high sensitivity and excellent repeatability and image uniformity.

While the invention has been described in detail and with reference to specific embodiments thereof, it will be apparent to one skilled in the art that various changes and modifications can be made therein without departing from the spirit and scope thereof.

What is claimed is:

1. An electrophotographic photoreceptor, wherein said photoreceptor is a laminated photoreceptor comprising a support having provided thereon a charge-generating layer containing a charge-generating compound and a charge-transporting layer contain an acetylene compound represented by formula (I):

$$Ar^1C\equiv C-Ar^3-C\equiv C-Ar^2 \tag{I}$$

wherein $Ar^1$ and $Ar^2$ each is an aromatic carbon ring or aromatic heterocyclic group; and $Ar^3$ represents an arylene group, divalent group derived from a condensed polycyclic aromatic group or group derived from a divalent aromatic heterocyclic group.

2. An electrophotographic photoreceptor as in claim 1, wherein $Ar^1$ and $Ar^2$ are individually selected from the aromatic carbon group consisting of phenyl, naphthyl, anthryl, pyrenyl, acenaphthenyl and fluorenyl.

3. An electrophotographic photoreceptor as in claim 1, wherein $Ar^1$ and $Ar^2$ are individually selected from the aromatic carbon group consisting of pyridine, thiophene, pyrrole, furan, benzofuran, benzothiophene, quinoline, carbozole, benzothiophene, and dibenzofuran.

4. An electrophotographic photoreceptor as in claim 1, wherein $Ar^3$ is selected from the group consisting of phenylene, naphthalene, anthrylene, biphenylene, and terphenylene, divalent groups derived from condensed polycyclic aromatic groups selected from the group consisting of indene, fluorene, acenaphthene, azulene, perylene, fluorenone, anthrone, anthraquinone, benzoanthrone, and isocoumarine, and divalent groups derived from aromatic heterocyclic groups selected from the group consisting of pyridine, quinoline, oxazole, thiazole, oxadiazole, benzoxazole, benzoimidazole, benzothiazole, benzotriazole, dibenzofurane, carbazole, phenothiazine, phenoxazine, and xanthene.

5. An electrophotographic photoreceptor as in claim 1, wherein said substituents for $Ar^1$, $Ar^2$ and $Ar^3$ are selected from the group consisting of alkyl groups having 1 to 18 carbon atoms, halogen atoms, cyano group, nitro group, hydroxyl group, carboxyl group, alkoxy groups having 1 to 18 carbon atoms, aryloxy groups having 6 to 14 carbon atoms, dialkylamino groups containing two $C_{1-8}$ alkyl groups, diarylamino groups containing two $C_{6-10}$ aryl groups, N-alkyl-N-arylamino groups containing $C_{1-8}$ alkyl group and $C_{6-10}$ aryl group, aryl groups having 6 to 14 carbon atoms, trialkylsilyl groups containing three $C_{1-6}$ alkyl groups, halogenoalkyl groups having 1 to 6 carbon atoms, and alkylthio groups having 1 to 6 carbon atoms, wherein if more than one substituent is present, the substituents may be the same or different, and wherein the substituents may be bonded to any carbon in $Ar^1$, $Ar^2$ and $Ar^3$.

6. An electrophotographic photoreceptor as in claim 1, wherein said photoreceptor is a laminated photoreceptor comprising a support having provided thereon, in order, a charge-generating layer containing a charge-generating compound and a charge-transporting layer containing an acetylene compound represented by formula (I).

7. An electrophotographic photoreceptor wherein said photoreceptor is a laminated photoreceptor comprising an electrically conductive support having provided thereon a charge-generating layer containing a charge-generating compound and an acetylene compound represented by formula (I), and a charge-transporting layer:

$$Ar^1C\equiv C-Ar^3-C\equiv C-Ar^2 \tag{I}$$

wherein $Ar^1$ and $Ar^2$ each is an aromatic carbon ring or aromatic heterocyclic group; and $Ar^3$ represents an arylene group, divalent group derived from a condensed polycyclic aromatic group or group derived from a divalent aromatic heterocyclic group.

8. An electrophotographic photoreceptor comprising an electrically conductive support having provided thereon a single light-sensitive layer containing both a sensitizing dye and an acetylene compound represented by formula (I), said layer containing no charge-generating compound:

$$Ar^1C\equiv C-Ar^3-C\equiv C-Ar^2 \tag{I}$$

wherein $Ar^1$ and $Ar^2$ each is an aromatic carbon ring or aromatic heterocyclic group; and $Ar^3$ represents an arylene group, divalent group derived from a condensed polycyclic aromatic group or group derived from a divalent aromatic heterocyclic group.

9. An electrophotographic photoreceptor as in claim 8, wherein $Ar^1$ and $Ar^2$ are individually selected from the aromatic carbon group consisting of phenyl, naphthyl, anthryl, pyrenyl, acenaphthenyl and fluorenyl.

10. An electrophotographic photoreceptor as in claim 8, wherein $Ar^1$ and $Ar^2$ are individually selected from the aromatic heterocyclic group consisting of pyridine, thiophene, pyrrole, furan, benzofuran, benzothiophene, quinoline, carbazole, benzothiophene, and dibenzofuran.

11. An electrophotographic photoreceptor as in claim 8, wherein $Ar^3$ is selected from the group consisting of phenylene, naphthalene, anthrylene, biphenylene, and terphenylene, divalent groups derived from condensed polycyclic aromatic groups selected from the group consisting of indene, fluorene, acenaphthene, azulene, perylene, fluorenone, anthrone, anthraquinone, benzoanthrone, and isocoumarine, and divalent groups derived from aromatic heterocyclic groups such as pyridine, quinoline, oxazole, thiazole, oxadiazole, benzoxazole, benzoimidazole, benzothiazole, benzotriazole, dibenzofurane, carbazole, phenothiazine, phenoxazine, and xanthene.

12. An electrophotographic photoreceptor as in claim 8, wherein said substituents for $Ar^1$, $Ar^2$ and $Ar^3$ are selected from the group consisting of alkyl groups having 1 to 18 carbon atoms, halogen atoms, cyano group, nitro group, hydroxyl group, carboxyl group, alkoxy groups having 1 to 18 carbon atoms, aryloxy groups having 6 to 14 carbon atoms, dialkylamino groups containing two $C_{1-8}$ alkyl groups, diarylamino groups containing two $C_{6-10}$ aryl groups, N-alkyl-N-arylamino groups containing $C_{1-8}$ alkyl group and $C_{6-10}$ aryl group, aryl groups having 6 to 14 carbon atoms, trialkylsilyl groups containing three $C_{1-6}$ alkyl groups, halogenoalkyl groups having 1 to 6 carbon atoms, and alkylthio groups having 1 to 6 carbon atoms, wherein if more than one substituent is present, the substituents may be the same or different, and wherein the substituents may be bonded to any carbon in $Ar^1$, $Ar^2$ and $Ar^3$.

13. An electrophotographic photoreceptor comprising an electrically conductive support having provided thereon a single light-sensitive layer comprising a charge-generating compound dispersed in a charge-transporting medium consisting of an acetylene compound and a binder, wherein said acetylene compound is represented by formula (I):

$$Ar^1C\equiv C-Ar^3-C\equiv C-Ar^2 \qquad (I)$$

wherein $Ar^1$ and $Ar^2$ each is an aromatic carbon ring or aromatic heterocyclic group; and $Ar^3$ represents an arylene group, divalent group derived from a condensed polycyclic aromatic group or group derived from a divalent aromatic heterocyclic group.

14. An electrophotographic photoreceptor as in claim 13, wherein $Ar^1$ and $Ar^2$ are individually selected form the aromatic carbon group consisting of phenyl, naphthyl, anthryl, pyrenyl, acenaphthenyl and fluorenyl.

15. An electrophotographic photoreceptor as in claim 13, wherein $Ar^1$ and $Ar^2$ are individually selected form the aromatic heterocyclic group consisting of pyridine, thiophene, pyrrole, furan, benzofuran, benzothiophene, quinoline, carbozole, benzothiophene, and dibenzofuran.

16. An electrophotographic photoreceptor as in claim 13, wherein $Ar^3$ is selected from the group consisting of phenylene, naphthalene, anthrylene, biphenylene, and terphenylene, divalent groups derived from condensed polycyclic aromatic groups selected from the group consisting of indene, fluorene, acenaphthene, azulene, perylene, fluorenone, anthrone, anthraquinone, benzoanthrone, and isocoumarine, and divalent groups derived from aromatic heterocyclic groups such as pyridine, quinoline, oxazole, thiazole, oxadiazole, benzoxazole, benzoimidazole, benzothiazole, benzotriazole, dibenzofurane, carbazole, phenothiazine, phenoxazine, and xanthene.

17. An electrophotographic photoreceptor as in claim 13, wherein $Ar^1$, $Ar^2$ and $Ar^3$ are selected from the group consisting of alkyl groups having 1 to 18 carbon atoms, halogen atoms, cyano group, nitro group, hydroxyl group, carboxyl group, alkoxy groups having 1 to 18 carbon atoms, aryloxy groups having 6 to 14 carbon atoms, dialkylamino groups containing two $C_{1-8}$ alkyl groups, diarylamino groups containing two $C_{6-10}$ aryl groups, N-alkyl-N-arylamino groups containing $C_{1-8}$ alkyl group and $C_{6-10}$ aryl group, aryl groups having 6 to 14 carbon atoms, trialkylsilyl groups containing three $C_{1-6}$ alkyl groups, halogenoalkyl groups having 1 to 6 carbon atoms, and alkylthio groups having 1 to 6 carbon atoms, wherein if more than one substituent is present, the substituents may be the same or different, and wherein the substituents may be bonded to any carbon in $Ar^1$, $Ar^2$ and $Ar^3$.

18. An electrophotographic photoreceptor as in claim 7, wherein $Ar^1$ and $Ar^2$ are individually selected form the aromatic carbon group consisting of phenyl, naphthyl, anthryl, pyrenyl, acenaphthenyl and fluorenyl.

19. An electrophotographic photoreceptor as in claim 7, wherein $Ar^1$ and $Ar^2$ are individually selected form the aromatic heterocyclic group consisting of pyridine, thiophene, pyrrole, furan, benzofuran, benzothiophene, quinoline, carbozole, benzothiophene, and dibenzofuran.

20. An electrophotographic photoreceptor as in claim 7, wherein $Ar^3$ is selected from the group consisting of phenylene, naphthalene, anthrylene, biphenylene, and terphenylene, divalent groups derived from condensed polycyclic aromatic groups selected from the group consisting of indene, fluorene, acenaphthene, azulene, perylene, fluorenone, anthrone, anthraquinone, benzoanthrone, and isocoumarine, and divalent groups derived from aromatic heterocyclic groups such as pyridine, quinoline, oxazole, thiazole, oxadiazole, benzoxazole, benzoimidazole, benzothiazole, benzotriazole, dibenzofurane, carbazole, phenothiazine, phenoxazine, and xanthene.

21. An electrophotographic photoreceptor as in claim 7, wherein $Ar^1$, $Ar^2$ and $Ar^3$ are selected from the group consisting of alkyl groups having 1 to 18 carbon atoms, halogen atoms, cyano group, nitro group, hydroxyl group, carboxyl group, alkoxy groups having 1 to 18 carbon atoms, aryloxy groups having 6 to 14 carbon atoms, dialkylamino groups containing two $C_{1-8}$ alkyl groups, diarylamino groups containing two $C_{6-10}$ aryl groups, N-alkyl-N-arylamino groups containing $C_{1-8}$ alkyl group and $C_{6-10}$ aryl group, aryl groups having 6 to 14 carbon atoms, trialkylsilyl groups containing three $C_{1-6}$ alkyl groups, halogenoalkyl groups having 1 to 6 carbon atoms, and alkylthio groups having 1 to 6 carbon atoms, wherein if more than one substituent is present, the substituents may be the same or different, and wherein the substituents may be bonded to any carbon in $Ar^1$, $Ar^2$ and $Ar^3$.

* * * * *